(12) United States Patent
Nambi et al.

(10) Patent No.: US 10,271,914 B2
(45) Date of Patent: Apr. 30, 2019

(54) MICROSURGICAL TOOL ADAPTERS, SYSTEMS AND RELATED METHODS

(71) Applicant: University of Utah Research Foundation, Salt Lake City, UT (US)

(72) Inventors: Manikantan Nambi, Salt Lake City, UT (US); Jacob J. Abbott, Salt Lake City, UT (US); Paul S. Bernstein, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 507 days.

(21) Appl. No.: 15/041,955

(22) Filed: Feb. 11, 2016

(65) Prior Publication Data
US 2016/0228205 A1 Aug. 11, 2016

Related U.S. Application Data

(60) Provisional application No. 62/176,258, filed on Feb. 11, 2015.

(51) Int. Cl.
| | |
|---|---|
| A61B 17/00 | (2006.01) |
| A61B 17/30 | (2006.01) |
| A61B 34/00 | (2016.01) |
| A61B 34/30 | (2016.01) |
| A61F 9/007 | (2006.01) |

(52) U.S. Cl.
CPC ............ *A61B 34/72* (2016.02); *A61B 34/30* (2016.02); *A61B 34/75* (2016.02); *A61B 2017/00477* (2013.01); *A61B 2017/00486* (2013.01); *A61B 2017/305* (2013.01); *A61F 9/007* (2013.01); *A61F 9/00727* (2013.01)

(58) Field of Classification Search
CPC ..... A61B 2017/305; A61B 2017/00486; A61F 9/00727
See application file for complete search history.

(56) References Cited

U.S. PATENT DOCUMENTS

| | | |
|---|---|---|
| 4,500,065 A | 2/1985 | Hennekes et al. |
| 4,611,377 A | 9/1986 | McCormick et al. |
| (Continued) | | |

FOREIGN PATENT DOCUMENTS

| | | |
|---|---|---|
| EP | 1647237 | 4/2006 |
| EP | 2574301 | 8/2016 |
| WO | WO2012/018816 | 2/2012 |

OTHER PUBLICATIONS

Nasseri et al, Robot-Assisted Microscopic Manipulation for Vitreo-Retinal Ophthalmologic Surgery; iRAM!S; http://www6.in.tum.de/Main/ResearchiRAM!S; Date Accessed Jan. 2016.

(Continued)

*Primary Examiner* — Terence Boes
(74) *Attorney, Agent, or Firm* — Thorpe North & Western, L.L.P.

(57) ABSTRACT

An adapter system can include a set of adapters operably adapted to a set of microsurgical tools. Each adapter in the set of adapters can be formed for a complimentary surgical tool in the set of surgical tools. Each adapter can have a setback feature designed to orient a corresponding tool tip at a common tip distance. An adapter receptacle can include a joint or joints having a rotary motion and/or translation mechanism and a setback stop feature.

23 Claims, 6 Drawing Sheets

(56) References Cited

U.S. PATENT DOCUMENTS

| | | | |
|---|---|---|---|
| 4,636,135 | A | 1/1987 | Bancoon |
| 4,979,949 | A | 12/1990 | Matsen, III et al. |
| 5,402,801 | A | 4/1995 | Taylor |
| 5,562,655 | A | 10/1996 | Mittelstadt et al. |
| 5,782,571 | A | 7/1998 | Hufford et al. |
| 6,190,395 | B1 | 2/2001 | Williams |
| 6,676,669 | B2 | 1/2004 | Charles et al. |
| 6,882,953 | B2 | 4/2005 | D'Hooge et al. |
| 7,066,940 | B2 | 6/2006 | Riedel et al. |
| 7,166,114 | B2 | 1/2007 | Moctezuma De La Barrera et al. |
| 7,661,162 | B2 | 2/2010 | Sorensen et al. |
| 7,730,563 | B1 | 6/2010 | Sklar et al. |
| 8,172,849 | B2 | 5/2012 | Noon et al. |
| 8,224,484 | B2 | 7/2012 | Swarmup et al. |
| 8,246,551 | B2 | 8/2012 | Miller et al. |
| 2006/0149194 | A1* | 7/2006 | Conston .......... A61B 17/32002 604/294 |
| 2007/0173790 | A1* | 7/2007 | Moctezuma De La Barrera ........ G16H 40/40 606/1 |
| 2009/0087249 | A1 | 4/2009 | Flagle et al. |
| 2009/0261536 | A1 | 10/2009 | Beale et al. |
| 2012/0041263 | A1 | 2/2012 | Sholev |
| 2013/0274765 | A1* | 10/2013 | Isaacson .......... A61B 17/12013 606/139 |
| 2013/0296882 | A1 | 11/2013 | Kim et al. |
| 2014/0018699 | A1* | 1/2014 | Rusnak .............. A61B 10/0233 600/566 |
| 2014/0142591 | A1 | 5/2014 | Alvarez et al. |
| 2017/0312004 | A1* | 11/2017 | Allen, IV ............... A61B 34/35 |

OTHER PUBLICATIONS

Intuitive Surgical, The Da Vinci Surgical System; https://www.intuitivesurgical.com/products/davinci_surgical_system/; Date Accessed Jan. 2016.

Farlas-Eisner et al, Da Vinci Robotic Surgery; Obstetrics and Gynecology UCLA; UCLA Health; http://obgyn.ucla.edu/da-vinci-robotic-surgery; Date Accessed Jan. 2016.

Wei et al, Design of Micro-Surgical Manipulators for Dual-Arm Microsurgery; Advanced Robotics and Mechanism Applications; A.R.M.A. Research Laboratory; http://research.vuse.vanderbilt.edu/arma/projects/Eye%20surgery/Eyesurgery.shmtl; Date Accessed Jan. 2016.

Iriss Intraocular Robotic Interventional and Surgical System; SurgRob; http://surgrob.blogspot.com/2014/10/iriss-intraocular-robotic.html; Date Accessed Jan. 2016.

Rahimy et al, Robot-Assisted Intraocular Surgery: Development of the IRISS and Feasibility Studies in an Animal Model; Eye; May 31, 2013; vol. 27 Issue 8; pp. 972-978.

Grace et al, Teleoperation for Ophthalmic Surgery: Form the Eye Robot to Feature Extracting Force Feedback; Automedica; 1998; vol. 16 Issue 4; pp. 293-310.

Taylor et al, Steady-Hand Eye Robot; Ciis; http://ciis.lesr.jhu.edu/dokuwiki/doku.php?id=research.eyerobots#people; Date Accessed Jan. 2016.

Schurle, Minimally-Invasive Eye Surgery on the Horizon as Magnetially-Guided Microbots Approach Clinical Trials; Robohub; http://robohub.org/minimally-invasive-eye-surgery-on-the-horizon-as-magentically-guided-microbots-move-toward-clinical-trials/; Jun. 26, 2013.

Riviere, Micron: Intelligent Microsurgical Instruments; Carnegie Mellon University The Robotics Institute; http://www.ri.cmu.edu/research_project_detail.html?type=description&project_id=32&menu_id=261; Date Accessed Jan. 2016.

MacLachlan et al, Micron: An Actively Stabilized Handheld Tool for Microsurgery; Transactions on Robotics; IEEE; Nov. 18, 2011; vol. 28 Issue 1; pp. 195-212.

Nasseri et al, The Introduction of a New Robot for Assistance in Ophthalmic Surgery; Engineering in Medicine and Biology Society (EMBC); IEEE; Jul. 2013; pp. 5682-5685.

Balicki et al, Single Fiber Optical Coherence Tomography Microsurgical Instruments for Computer and Robot-Assisted Retinal Surgery; Medical Image Computing and Computer-Assisted Intervention; MICCAI; Sep. 2009; pp. 108-115.

* cited by examiner

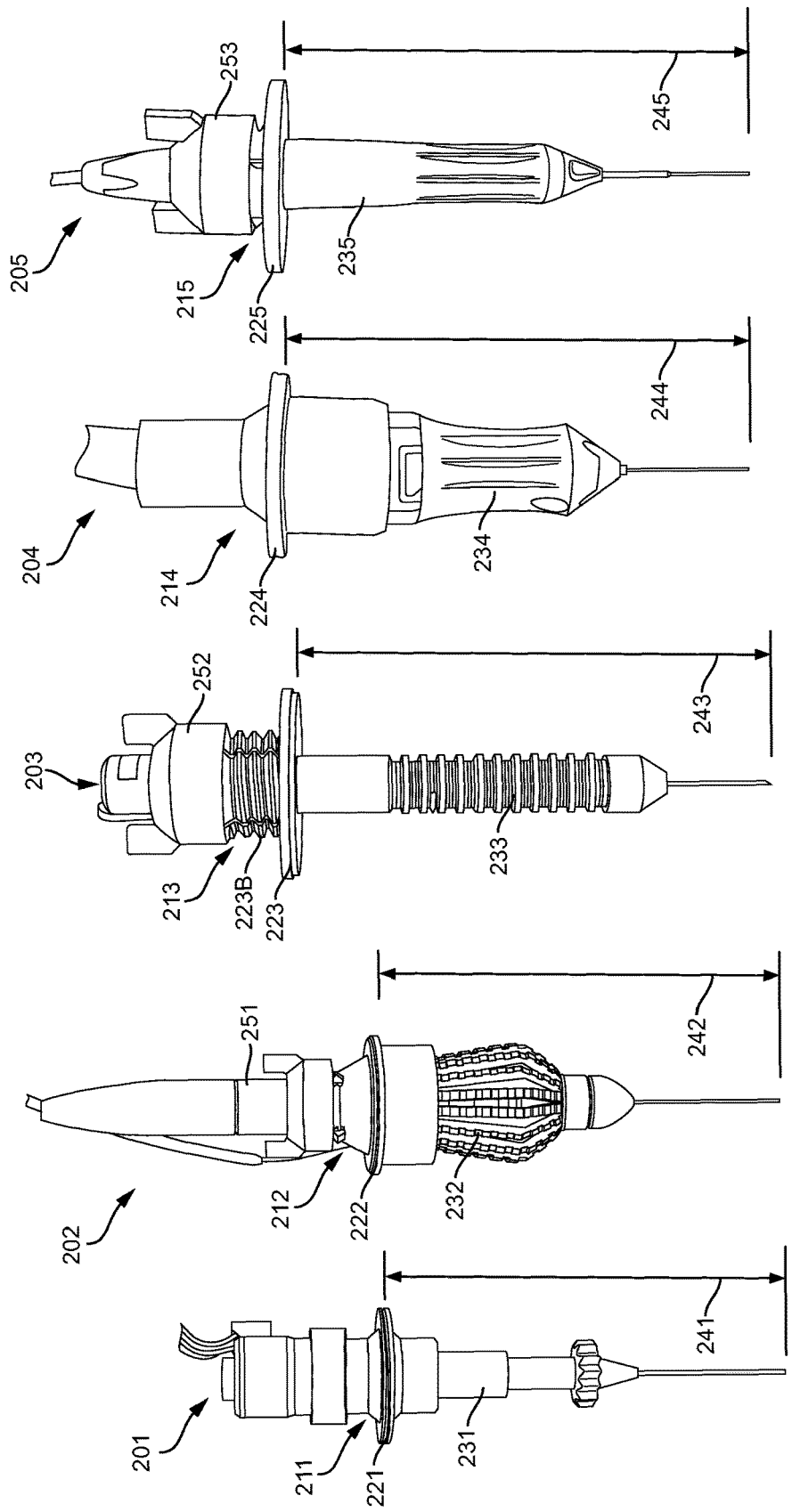

MICROSURGICAL TOOL ADAPTERS, SYSTEMS AND RELATED METHODS

RELATED APPLICATION

This application claims priority to U.S. Provisional Application No. 62/176,258, filed Feb. 11, 2015, which is incorporated herein by reference.

BACKGROUND

Various types of surgeries utilize precision instrumentation and robotics. Despite significant advancements, such instrumentation presents challenges, especially as applied to the use of surgical tools in delicate, or generally difficult, operations. For example, it has been shown that certain aspects of traditional retinal microsurgery procedures are at or beyond the limits of human precision. In some examples of traditional retinal microsurgery, an error of only a few micrometers can cause a surgical instrument to exert damaging force on the retina, causing localized loss of vision, increased chances of infection, or other complications. The forces experienced during retinal surgeries can be below what surgeons can feel (<7 mN), and, therefore, surgeons must rely on visual feedback only. The surgeon pivots the instruments about the scleral trocars, limiting dexterity, and uses the instruments to manipulate the eye to provide better imaging through a corresponding surgical microscope. Patient movement due to breathing must also be accounted for by the surgeon, and in addition, among patients who snore under monitored anesthesia (indicated to be in ≈16% of cases), half have sudden head movements during surgery, leading to a high risk of complications.

One of the most difficult retinal-surgery procedures involves the peeling of membranes on the retina. Epiretinal membrane (ERM) comprises sheets of fibrous tissue up to 61-µm thick that can distort macular anatomy and disturb vision after posterior vitreous detachment or retinal tears, and the inner limiting membrane (ILM) is a naturally occurring 0.15-4-µm thick membrane that can contract with age and generate macular holes. To improve vision in affected eyes, ERM and ILM are peeled by inserting delicate instruments inside the eye. Membrane peeling is a delicate procedure, and complications can occur in the form of intraoperative hemorrhage, retinal detachment during or after surgery, infection after surgery, regrowth of epiretinal membrane, and increased rate of cataract development. In some cases, a second surgery is required to remove fragments of the ERM/ILM left behind. Other experimental procedures inside the eye like retinal vein cannulation involve delivering drugs to retinal veins that measure less than 100 µm in diameter, whereas physiological tremor in the human hand during retinal surgery was measured to be 100 µm. In such surgeries, instruments are inserted through the trocars in the pars plana region of the sclera and are used to perform delicate scraping and peeling motions to peel membranes on the retina.

There are opportunities for significant improvement in retinal-surgery procedures in terms of safety and consistency of outcomes. As our population ages over coming years, the number of surgical procedures will likely increase relative to the number of surgeons available. Robot-assisted retinal surgery will enable surgeons to improve surgical efficiency by enabling them to overcome their human limitations, extend their working life, and capitalize on their experience even after their manual dexterity abilities have diminished.

Prior research in robot-assisted retinal surgery has resulted in the development of telemanipulated systems and cooperative manipulators. Robotic systems for retinal surgery have typically been relatively large and stiff, and thus table-mounted. In related work, active hand-held instruments primarily aimed at tremor reduction, with no ability to affect the "DC" system response, have been shown to reduce RMS tremor to 10 µm-60 µm. Since the human hand is the source of tremor during microsurgery, telemanipulated systems, which eliminate direct contact between the surgeon and the instrument, seem particularly promising. Most prior systems can leave the retina at risk in the event of sudden head movement, and rhythmic head movements would need to be actively compensated. Notable exceptions are the TU Munich and Columbia/Vanderbilt systems, which are designed to be patient head-mountable. The TU Munich system has been demonstrated to be head-mountable.

SUMMARY

Examples of adapters and systems related to robotically assisted surgical devices and replaceable tools are disclosed herein. One example of an adapter system includes a set of adapters operably adapted to a set of micro surgical tools. Each adapter in the set of adapters can be formed for a complimentary surgical tool in the set of surgical tools. Each adapter can have a setback feature designed to orient a corresponding tool tip at a common tip distance.

An adapter receptacle is also disclosed herein. The adapter receptacle can include a joint having a rotary motion translation mechanism and a setback stop feature. The adapter receptacle can singly receive each adapter to allow exchange of adapters and corresponding tools during surgery.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

FIG. 2A is a perspective view of a microforceps tool with an adapter according to examples of the present disclosure.

FIG. 2B is a perspective view of another microforceps tool with another adapter according to examples of the present disclosure.

FIG. 2C is a perspective view of yet another tool (diamond-dusted membrane scraper—DDMS) with yet another adapter according to examples of the present disclosure.

FIG. 2D is a perspective view of a vitrector tool with still another adapter according to examples of the present disclosure.

FIG. 2E is a perspective view of a light probe tool with yet still another adapter according to examples of the present disclosure.

Figure 1A:
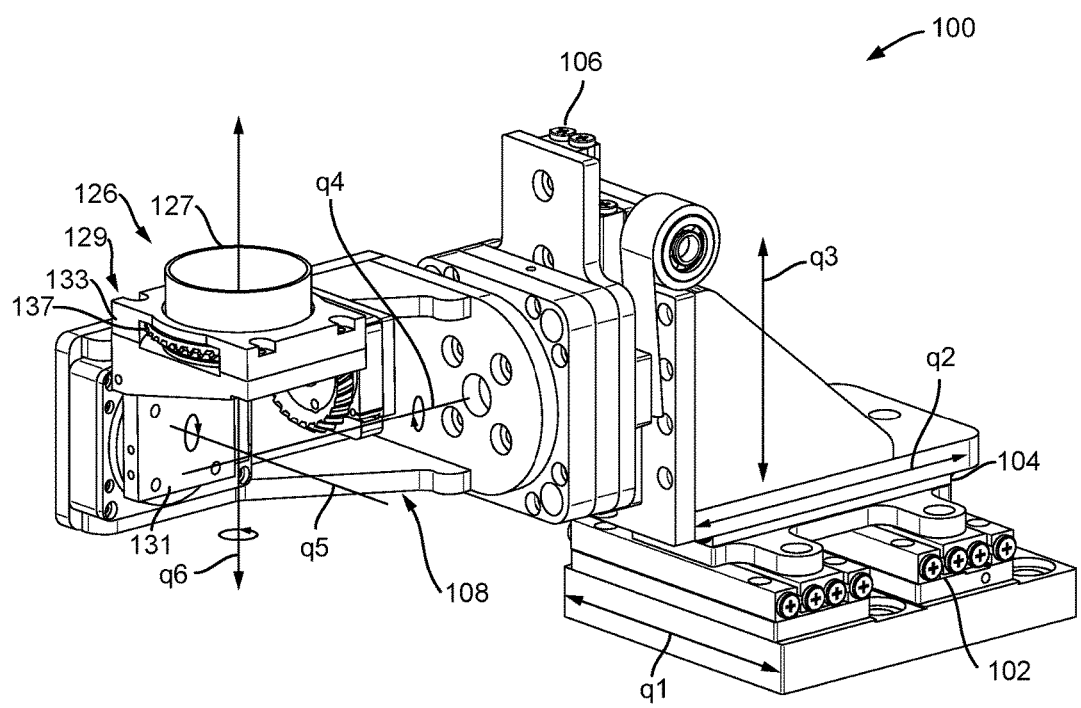
FIG. 1A is a perspective view of a manipulator including a rotary actuator and receptacle according to examples of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "an interface" includes reference to one or more of such features and reference to "rotating" refers to one or more such steps.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each (e.g. A+B, B+C, A+C, and A+B+C).

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Microsurgical Tool Adapter

Although microsurgical robotic systems provide significant advantages, continued improvements can further enhance performance and reliability of patient outcomes. For example, it has been recognized by the inventors there is a need for simple and consistent replacement of multiple types of tools during various types of surgery. Unfortunately, many microsurgical tools have significant variations in length which requires a physician to spend excessive amounts of time retracting the tool away from relevant tissue (e.g. from several mm to several centimeters). Upon replacement, the manipulator holding the new surgical tool must then be reintroduced to the relevant patient tissue. Accordingly, adapters and corresponding adapter receptacles can include setback features which orient tool tips at a common distance. In this manner, the tools can be retracted only a modest distance (e.g. less than 2-4 mm) from the tissue to allow replacement of tools which have different lengths while maintaining a common tip distance relative to a robotic manipulator position.

Examples according to the present disclosure can be operable with a manipulator for retinal surgery that utilizes piezoelectric stick-slip actuators, which are designed specifically for micromanipulation. Piezoelectric stick-slip actuators have a high resolution (<1 nm) and a high dynamic displacement range (cm-nm). During normal operation these actuators behave like admittance-type devices (i.e., they are stiff, they passively remain in place until actively commanded to move, and they are stationary in the event of power loss), yet they can be back-driven with a gentle force by a human hand (or any other applied force) with no damage to the device, which is significantly different behavior than a traditional admittance-type device.

An exemplary manipulator system as described herein has submicron resolution and is small and light enough to be head-mounted (as one of ordinary skill would appreciate for uses related to examples herein as well as others). The manipulator system is compact and light enough that it can be made head-mounted to passively compensate for head movements. Also described is an adapter that enables the use of the full range of unmodified commercially available microsurgical instruments, including instruments that require some form of actuation, such as, but not limited to, microforceps and scissors, and non-actuated instruments, such as, but not limited to, a diamond-dusted membrane scraper (DDMS), a vitrector, a fiber-optic light, keratomes, loops, needles, trocar, cannulas, backflush, spatula, laser probe, foreign body and magnet. Commercial manufacturers for such tools include, but are certainly not limited to, Alcon, Synergetics, Dutch Ophthalmic. The instrument adapter also enables quick change of instruments, which is useful in retinal surgery, for example.

Figure 1B:
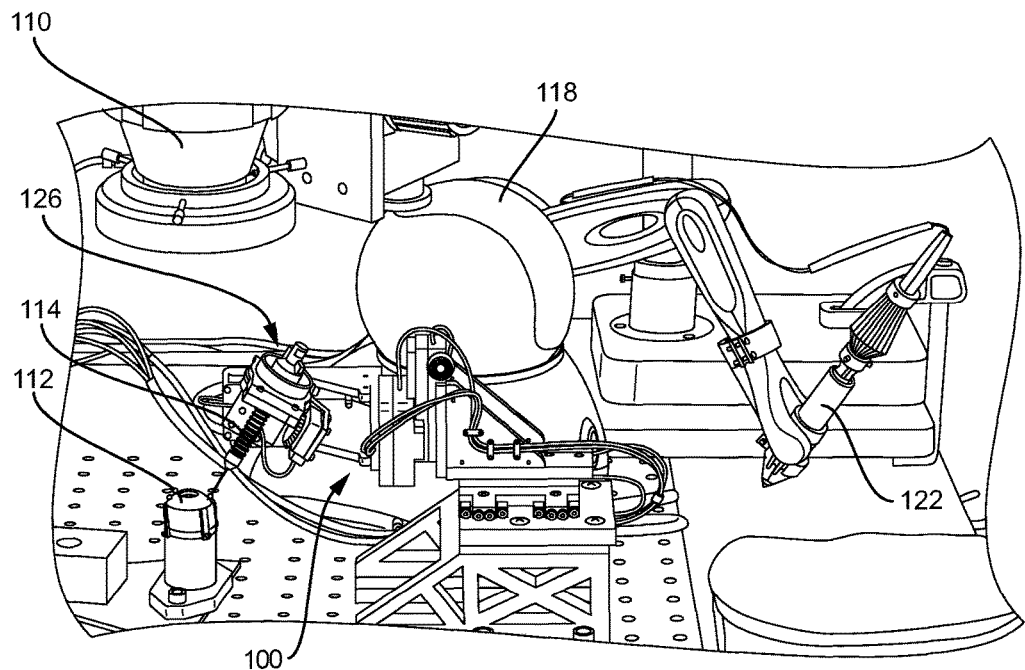
FIG. 1B is a perspective view of a telerobotic microsurgery system including a manipulator, operator stylus, rotary actuator, a receptacle, an adapter, and a tool according to examples of the present disclosure.
Figure 1C:
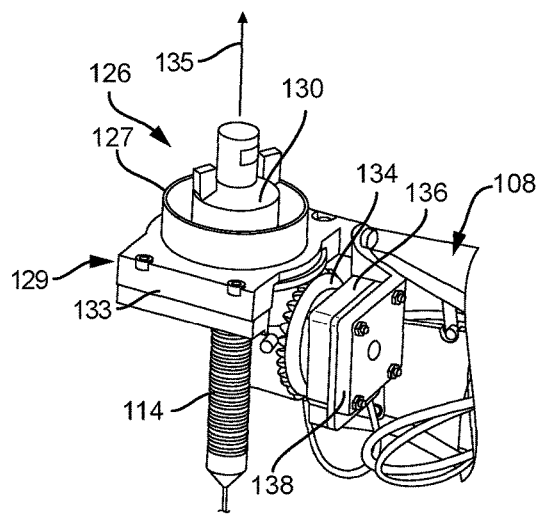
FIG. 1C is a perspective view of a portion of a system including a rotary actuator, a receptacle, an adapter, and a tool according to examples of the present disclosure (shown also, in part, in FIG. 1B).

Referring to FIGS. 1A-1C, a six-degree-of-freedom (6-DOF) telerobotic manipulator system 100 for retinal surgery was designed using off-the-shelf piezoelectric stick-slip actuators 102, 104 and 106 from SmarAct GmbH as shown best in FIG. 1A. The linear actuators 102, 104 and 106 move a manipulator arm 108 along axes q1, q2, and q3, respectively, to provide 3-DOF linear translation movement. The manipulation system 100 (or manipulator) for retinal surgery can use a full range of unmodified commercially available instruments via a corresponding complimentary adapter 130 and adapter receptacle 127.

FIG. 1B depicts an experimental setup of the system 100 used in a laboratory in-vitro retinal-surgery arrangement. In a surgical operation, a surgeon looks in the phantom eye 112 (or patient eye when performing surgery on a live patient) using a stereo microscope 110. The surgeon then telemanipulates the end-effector of the instrument 114 with 4-DOF (3-DOF translation, and rotation of the instrument about its axis) using an operator haptic input device 118 (located to enable direct access to instruments). Alternatively, a 6-DOF manipulator can be utilized to control the end-effector of the instrument 114 with 4-DOF while independently controlling the location of the trocar with 2-DOF, in order to perform orbital manipulation of the eye. In one example, the operator haptic input device can be a Geomagic Touch, although other haptic input devices can be used. A custom stylus 122 can also be operably connected to the haptic input device 114.

FIG. 1C depicts the yaw joint 126 of the manipulator 100, which enables rotation of the instrument about its axis, with an adapter 130 that allows instruments to be attached to the manipulator 100 via coupling with an intermediate adapter receptacle 127. The adapter receptacle 127 can also be secured to the manipulator arm 108 via a receptacle retention platform 129. The receptacle retention platform 129 can allow the adapter receptacle to freely rotate within the platform 129 while also providing minimal (e.g. less than a few microns) play between the receptacle and the platform. In the illustrated example, the receptacle retention platform 129 includes a base portion 131 which connects to the manipulator arm 108 and a receptacle housing portion 133 which rotatably retains the adapter receptacle 127. Further, substitutions to various components may be possible as would be understood by one of skill in the art. For example, the yaw joint 126 can also be a linear actuator for an alternate degree of freedom in the tool. In another example, the receptacle retention platform 129, which includes the yaw joint 126, can also be mounted on a linear actuator to provide an additional degree of freedom proximal to the final yaw joint 126, which can be utilized to perform a pure insertion or retraction of the instrument into or out of the eye. In examples, the manipulator 100 can include the yaw joint 126 provided as an integral component to the manipulator 100. Further, the yaw joint 126 can have the adapter stop (discussed further below) formed integrally therewith.

With particular reference to FIG. 1A, the exemplary manipulator 100 comprises a 3-DOF translation stage and a 3-DOF spherical wrist, which enables the manipulator 100 to position the instrument 114 inside a 20-mm-diameter spherical-section bowl centered on the retina with a virtual remote center on the surface of the eye (a sphere of 25.4-mm diameter). The linear stages 102, 104 and 106 corresponding to axes q1, q2, and q3, respectively, can in one example have a range of 40 mm with a closed-loop resolution of 100 nm. Stage 102 utilizes a parallel-rail structure, in which one rail is a stick-slip actuator and the other is a passive guide. The vertical direction (q3) includes a constant-force spring to offset the weight of the spherical wrist. In this example, the spherical wrist comprises three rotary piezoelectric stick-slip actuators, with a closed-loop resolution of 25 microdegrees for the roll (q4) and pitch (q5) actuators, and with a yaw actuator that enables open-loop rotation about the axis of the instrument (q6) with a resolution of 3 millidegrees. The positioning precision of the manipulator 100 is measured with joint sensors while performing constrained motion near the retina to be <1 μm, and the maximum velocity at the end-effector is 6 mm/s. The positioning precision was verified using a VHX-5000 (Keyence Corp.) microscope. The linear actuators of the manipulator 100 (SmarAct SLC-2460) can be backdriven by applying a force of 5 N, and the roll and pitch rotary actuators (SmarAct SR-4513, SR-2812) can be backdriven by applying torques of 15 N-cm and 6 N-cm, respectively. The maximum force that the linear actuators can apply while in motion is 4 N, and the roll and pitch actuators can apply a torque of 6 N-cm and 3 N-cm, respectively. In an example, the manipulator 100 measures 200×100×70 mm3 and weighs 0.8 kg. Variations in actuator models and specifications can be made based on availability, desired resolution, speed, torque, and other well-known design criteria for microsurgical robotic systems.

The manipulator 100 was manufactured to instructed specifications, and the yaw joint 126 of the manipulator 100 was further modified such that it can use a wide range of actuated and non-actuated instruments. The modified yaw joint 126 can be manufactured using a 3D printer (e.g. Objet Eden260), although such parts can be formed via molding, machining, or any suitable part manufacturing method. The yaw joint 126 is designed with the yaw actuator's axis (q5)

orthogonal to the instrument's axis (q6), and the rotary motion to the instrument is transmitted using spiral bevel gears 134 which are rotated using rotary actuator 136. The spiral bevel gear 134 in this example includes a 23-mm aperture and has internal threads that enable instruments to be attached to the manipulator 100 via the corresponding adapter receptacle 127. An aperture size of the receptacle can be selected such that disposable instruments of a wide range of form factors can be used with the manipulator 100. It is to be understood that other manipulators may be used in conjunction with the adapters and systems thereof according to the present disclosure. Rotary motion from the bevel gear 134 is transmitted to a complimentary gear set 137 oriented about a periphery of adapter receptacle 127. In this manner, a corresponding instrument or tool 114 can be rotated about a tool axis (q6) when secured to the adapter receptacle 127.

It is to be understood that various aspects of the experimental manipulator 100 can be provided or used in a subset or individual capacity. For example, spiral bevel gear 134, adapter receptacle 127, and receptacle retention platform 129 can be provided as a disposable kit. This can facilitate placement of a surgical drape or curtain between the rotary actuator 136 and the spiral bevel gear 134, as well as between the base portion 131 of the receptacle retention platform 129 and the manipulator arm 108. In one alternative aspect, the base portion 131 and bevel gear 134 can be secured in place using magnetic couplings. For example, complimentary permanent magnets can be placed on the rotary actuator 136 and the bevel gear 134, and/or between the base portion 131 and the manipulator arm 108. In this way, the protective sheet can be placed therebetween while also allowing movement during use. Such an approach can maintain a sterile and isolated environment between the patient and robotic manipulator. In this case, the disposable kit can be formed of a suitable plastic (e.g. ABS, PDMS, polyacrylates, etc). Alternatively, these parts can be formed of reusable materials such as, but not limited to, metals (e.g. aluminum, steel, alloys, etc), plastics, composites (carbon fibers, ceramics, etc), and the like.

From observations in an operating room, it has been found that during retinal surgery, on average, the surgeon changes the instrument every two minutes. It is therefore important that a robotic system for such procedures facilitates the quick change of instruments without disturbing the flow of the procedure. In examples, an adapter enables the surgeon to change instruments frequently, and enables the use of disposable instruments that require "pinch-grip" actuation such as microforceps and scissors, with this seventh DOF of actuation connected to the instrument rather than to the manipulator. Notably, as can be seen in FIG. 1C, the instrument 114 (and coupled adapter 130) are removed from the adapter receptacle 127 in a direction 135 along tool axis q6 from an upper side of the receptacle which is away from patient tissue.

An example system utilizes a set of adapters that are attached to corresponding disposable instruments before surgery. An adapter system according to the present disclosure can include a set of adapters operably adapted to a set of microsurgical tools. These adapters can be removably coupled to corresponding instruments or integrally formed as part of the instruments. Removable adapters allow a surgeon to dynamically choose whether to use particular tools manually or with the robotic system. An example set of tools with corresponding removable adapters is shown in FIGS. 2A-2E. Depicted are examples of disposable retinal-surgery instruments 201 (SYNERGETICS microforceps tip), 202 (ALCON microforceps), 203 (DDMS), 204 (vitrector), 205 (light probe) with corresponding adapters 211, 212, 213, 214, 215 that enable quick-change mounting to the exemplary 6-DOF manipulator 100. Each adapter 211, 212, 213, 214, 215 in the set of adapters can be formed for a complimentary surgical tool 201, 202, 203, 204, 205 in the set of surgical tools. The length of each instrument is known, and the distance from the adapter base (see, e.g., FIG. 2F adapter base 226) to the tip of the instrument is kept within a common tip distance for each instrument. Typically the common tip distance is within about 200 μm, often within about 100 μm, and in some cases within 50 μm across adapter-tool combinations within the set. More specifically, each adapter 211, 212, 213, 214, 215 includes a setback feature 221, 222, 223, 224, 225 designed to orient a corresponding tool tip at a common tip distance. The adapters can be designed such that the shape of the adapters conforms to the shape of a specific instrument (see FIG. 2C and FIG. 2F) maintaining a constant and repeatable distance between the instrument tip and the adapter base. For example, the distances as shown at 241, 242, 243, 244, 245 provide a consistent depth from the tip of the tool 231, 232, 233, 234, 235 to the setback feature 221, 222, 223, 224, 225. In an example, a distance of 84.5 mm has been shown with various instruments, which was largely determined by design for use with an Alcon microforceps (see, e.g., FIG. 2B). In this example, the Alcon microforceps had a larger form factor relative to other tools used in a surgical procedure to ensure interoperability of system components from one adapter to another.

Regardless, in each case, the setback feature can further include a tool engagement feature which retains the corresponding tool within the adapter at the desired distance. The tool engagement feature can be any feature which retains a tool within the adapter at a fixed distance to achieve the desired tool tip distance. Non-limiting examples of tool distance engagement features can include a radial protrusion, tapered inner adapter surfaces, inner adapter surface ledges, clips, and the like. For example, in FIG. 2A the microforceps have an external profile with a lip. A corresponding ledge can be formed on an internal surface of the adapter which engages with the lip at a fixed distance. With reference to FIG. 2B, the microforceps have a gradually widening profile near a mid-portion of the tool. An internal tool engagement surface of the adapter can have a corresponding tapered profile which engages with the widening profile to create an interference fit at the desired distance. The interference fit can optionally be further tightened using a locking nut 251. Thus, the setback control feature can include complimentary features which are specific to the corresponding tool which fix the tool tip distance within a desired distance.

Figure 2F:
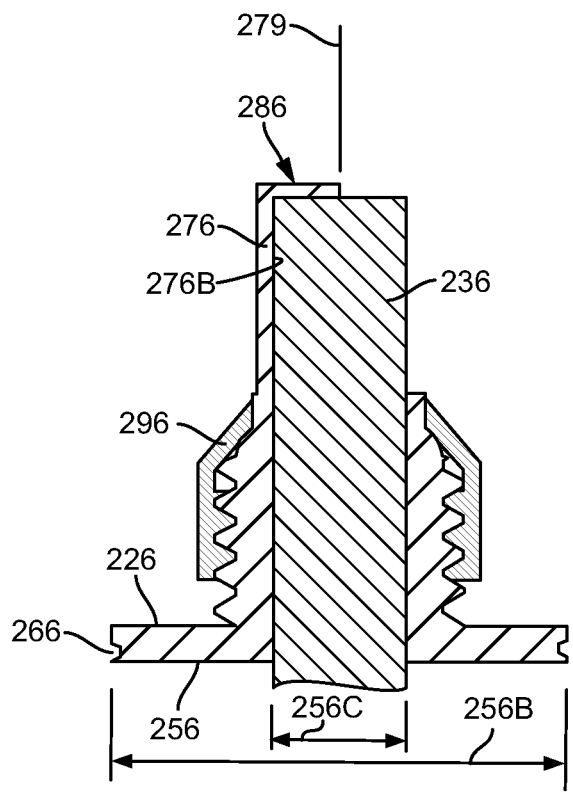
FIG. 2F is a cutaway cross sectional view of an adapter as used with a tool as shown in FIG. 2C.
Figure 2G:
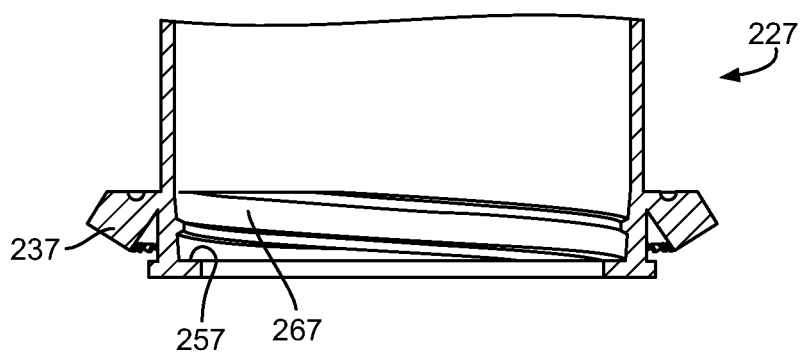
FIG. 2G is a cutaway cross sectional view of a receptacle according to examples of the present disclosure.

Referring now to FIG. 2G, the adapter system can include an adapter receptacle 227 having an operational connection mechanism to attach the adapter to the receptacle 227 with the common tip distance. In an example shown in FIG. 2F, at least one of the adapters in the set of adapters includes a sleeve 276 having a tool engagement surface 276B and an adapter receptacle interface 266. As shown in FIG. 2F, the setback feature can include a radial protrusion 286 extending inwardly from a sleeve 276 along a primary axis 279 of the adapter. In this manner, a back end of the tool 236 does not pass beyond the protrusion 286. In other examples, the setback feature can be a radial intrusion extending toward a primary axis of the adapter at any point along the tool. Further, the radial protrusion can be a constricted inner surface corresponding to an outer surface of the tool. In some cases, a cross-sectional area of the tool can have progressively increasing size, e.g. a tapered outer shape. In such cases, the setback feature can be a constricted opening (e.g. tapered, staged ledges, etc) through which the tool cannot pass beyond the common tip distance.

As shown in FIG. 2F, the adapter 226 includes an adapter receptacle interface 256. The female threads, shown at the receptacle interface 266, operably interface with the male threads 267 of the receptacle 227 of FIG. 2G. In an example, the adapter can have an inner diameter 256C and an outer diameter 256B each dimensioned such that the adapter 226 is operably connectable to the tool 236 and to the yaw joint. In another example, the tool engagement surface is formed of multiple flexible parallel tabs (e.g., 223B of FIG. 2C) circumferentially oriented about a tool location to engage the corresponding tool via an outer fastening compression nut 296 (251 of FIG. 2B, 252 of FIG. 2C, or 253 or FIG. 2E). Gaps between tabs allow the tabs to resiliently flex against the tool outer surface as compression nut 296 is tightened. In another example, at least one of the adapters in the set of adapters is segmented to be compressed for applying a retention force on the tool for actuation thereof. In still another example, the adapter receptacle interface includes an annular disk having complimentary threads 266 that threadingly engage with threads 267 of a receptacle 227. The adapter can use a threaded engagement inspired by Luer fittings as an example of a threaded engagement for this type of arrangement, while other engagements, threaded and non-threaded can be used. For example, a bayonet, BNC, or similar connector can be used. Non-limiting examples of suitable engagements can include detents, ball detent coupling, spring rack connector, flange clips, and the like. It is to be understood that the tool can be any instrument used as an end-effector with telerobotic devices. In some examples, each adapter can be integrally formed with each complimentary tool. In other examples, each adapter can be removably coupleable with each complimentary tool.

In one example, an adapter system can include a first rotary input mechanism operably connected to a base plate (e.g. 138 in FIG. 1C). In an example, the base plate is operatively connected to the manipulator 100. However, it is to be understood that the base plate may be attached to other fixed structure of an alternate manipulator device. The first rotary input mechanism can receive a rotational input for transmission to a second rotary input mechanism 237. The first rotary input mechanism may be any rotary actuator. Further, the second rotary input mechanism 237 can be arranged to translate the rotational input from the first rotary input mechanism to a tool rotation axis (e.g. q6). In an example the first and second rotary input mechanism can be a spiral bevel gear set. It is to be understood that one or more of the first rotary transmission mechanism, the base plate, and interfacing components therebetween comprise a disposable polymer material.

An adapter stop or setback feature on the adapter enables the instrument to be attached in the intended position with a repeatable common tip distance. Once the instruments with the adapters are attached to the manipulator, the end-effector of any instrument will be at the same known location within a small tolerance (80 μm measured using images). In some examples, the tolerance for the common tip distance can be less than 1 mm among the set of adapters, in some cases less than 500 μm, and in other cases less than 200 μm.

To characterize the instrument change time for an exemplary manipulator, a simple experiment was performed with five subjects in which the subjects changed the instrument from a DDS to a microforceps and then back to a DDS (5 trials), at a comfortable speed. The time required to change an instrument was found to be 12.7 s±2.5 s (mean±standard deviation).

This experiment was repeated with the same instruments for a manual surgery, and found an average change time of 8.3 s±1.4 s. With an increase in time of 5 seconds for every 2 minutes of surgery (a 4% increase), it was concluded that the additional time due to tool change is fairly insignificant. By recording the joint sensor values, it was confirmed that there was no motion in the joints while the instrument was being changed. Hence the instruments can be changed while the end-effector is still positioned inside the eye without a risk of injuring the retina due to unintended motions during instrument change. The end-effector can optionally be retracted some small retraction distance in order to avoid inadvertent damage. Typically a retraction distance of about 0.5 mm to 5 mm, and in some cases from 1 mm to about 3 mm, is sufficient. However, alternative methods can be used to register the exact location of the tool tip with respect to tissue in each case.

Sterilizability is an important consideration for manipulators used in surgery. The exemplary manipulator is small enough that the entire manipulator can be gassed or autoclaved between procedures (SmarAct makes autoclavable actuators). Alternatively, all components distal to the rotary actuator 136 shown in FIG. 1C can be made disposable or removable for autoclaving. This would enable the remainder of the manipulator to be wrapped in sterile draping with a pass through for a rotary actuator's shaft, using a method inspired by that employed by Intuitive Surgical's da Vinci. Additionally, it has also been verified that surgical draping can be inserted between the quick-change adapter and the spiral gear on the manipulator to which the adapter is attached (FIGS. 2F and 2G), and can be inserted between the linear stepper motor and the disposable microforceps tip (FIG. 3A) without affecting operation of the plunger, providing a potential alternate path to sterilization.

Actuation Mechanisms for Instruments

Two different actuation mechanisms were designed to enable the use of two different families of actuated instruments commonly used in retinal surgery: disposable instrument tips (e.g., Synergetics microforceps tip (FIG. 2A)) that are used with reusable handles, and completely disposable instruments (e.g., Alcon microforceps (FIG. 2B)). However, any such microsurgical instruments can be used as previously described.

EXAMPLES

Actuation with Stepper Motor

Figure 3:
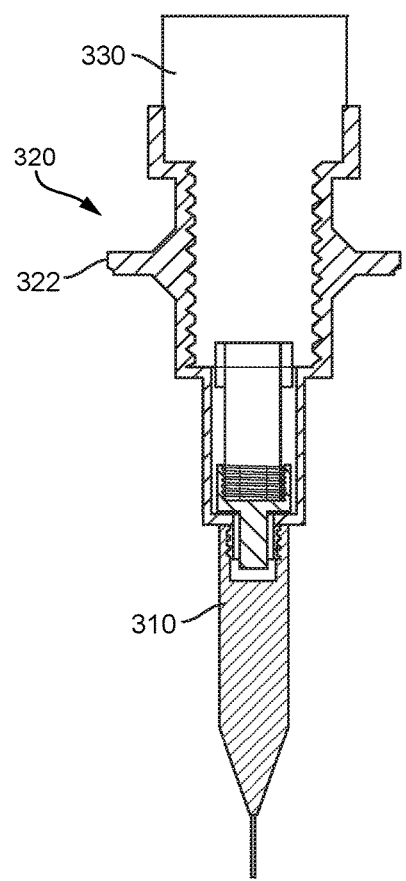
FIG. 3 is a cross-sectional view of a tool and an adapter according to examples of the present disclosure.

FIG. 3 is a section view of a Synergetics microforceps tool 310 actuated by a linear stepper motor 330 with an adapter 320 according to the present disclosure. The adapter further includes an adapter receptacle interface 322 sized to couple with a corresponding receptacle (e.g. FIG. 2G). In an example, which involves actuating a disposable instrument tip by pressing a plunger on the device, a linear stepper motor (LC15, HaydonKerk) was used with force capability of 5 N (2 N is required to actuate a Synergetics microforceps). The stepper motor was attached to the microforceps tip using an adapter that enables the microforceps to be mounted on the manipulator (FIG. 3). The LC15 has a linear resolution of 2.5 μm, and requires 500 steps (travel of 1.25 mm) for the complete actuation (i.e., fully open to fully closed) of the microforceps. The bandwidth (measured by video analysis) for a full open-close cycle of the microforceps with the stepper motor was 2.5 Hz.

Actuation with Soft Actuator

Figure 4A:
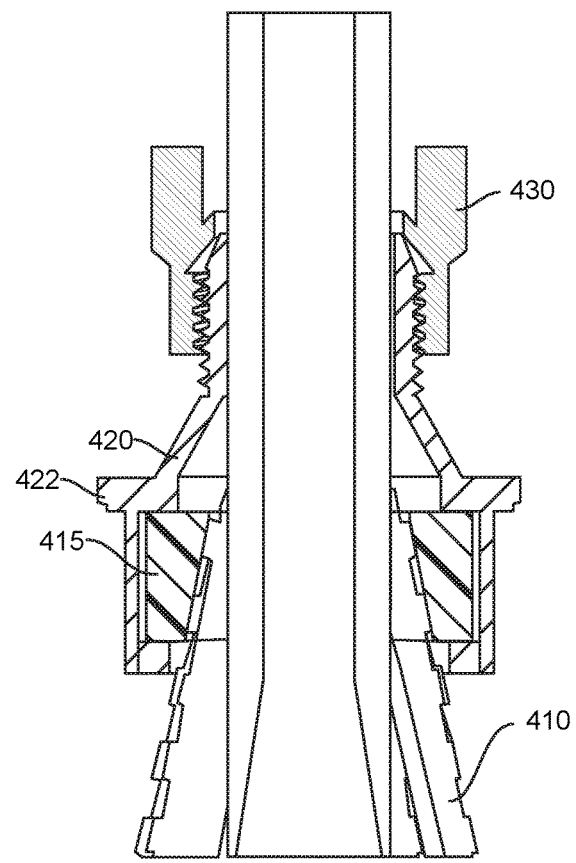
FIG. 4A is a cutaway cross-sectional view of another tool and another adapter according to examples of the present disclosure.
Figure 4B:
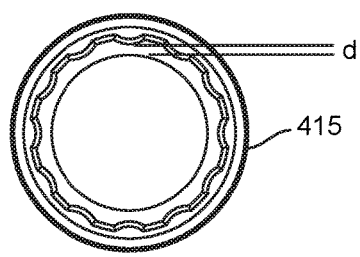
FIG. 4B is a cross-sectional view of an actuator mechanism component according to examples of the present disclosure.
Figure 4C:
FIG. 4C is a perspective cut-away view of an actuator mechanism component according to examples of the present disclosure.
Figure 4D:
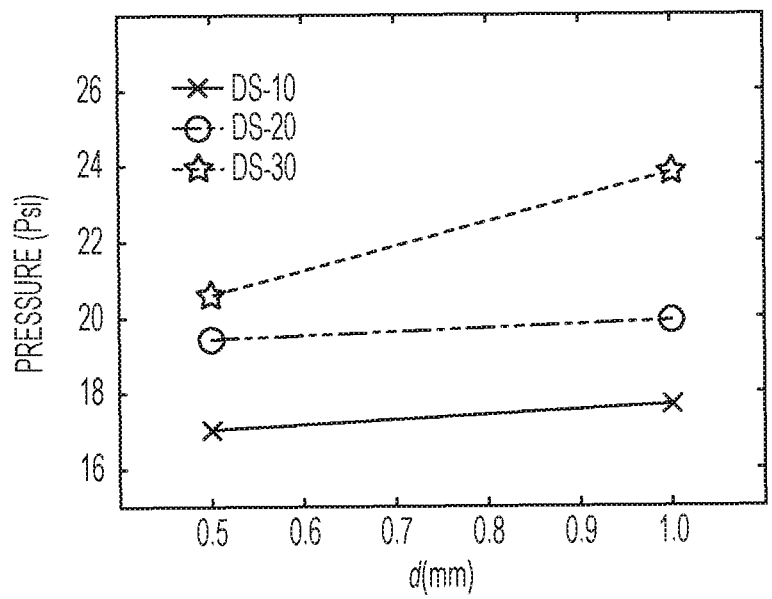
FIG. 4D is a graph of pressure against distance with DS-10, DS-20, and DS-30 according to examples of the present disclosure.
Figure 4E:
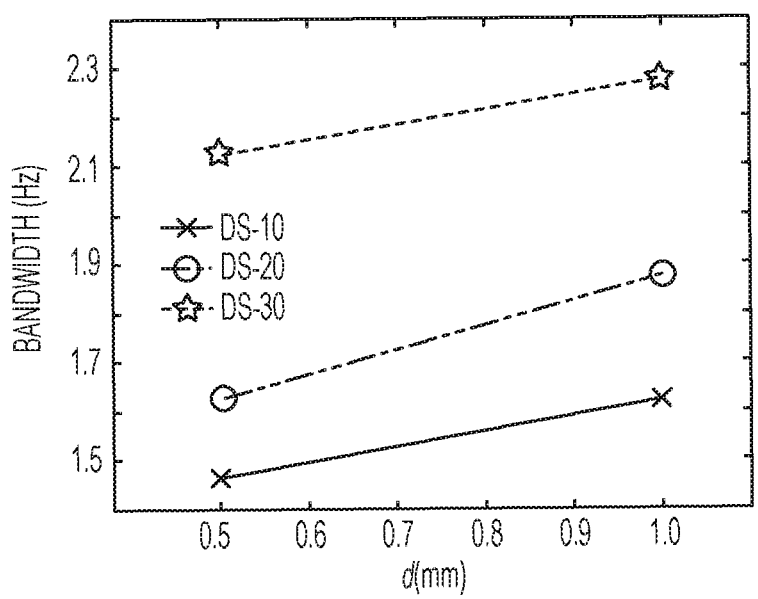
FIG. 4E is a graph of bandwidth against distance with DS-10, DS-20, and DS-30 according to examples of the present disclosure.

FIG. 4A depicts a section view of an Alcon microforceps tool 410 actuated by a soft actuator 415 with an adapter 420 according to the present disclosure. AS with other examples, the adapter also includes an adapter receptacle interface 422 which is removably coupleable with a corresponding adapter receptacle. The second actuation mechanism, for use with completely disposable Alcon instruments, uses a soft actuator 415 inspired by a blood-pressure cuff, which squeezes the ribs on a pinch-grip device when supplied with pressurized air (already available in the operating room). FIG. 4B depicts a top section view of the soft actuator 415. The paper sheath on the outer wall and the profile of the inner wall only allow for expansion radially inward. The soft actuator is molded from a silicone elastomer using soft-lithography techniques. 3D-printed molds with inserts are used in a two-step process to fabricate the soft actuator that has a channel for pressurized air, which was then heat cured at 70 degrees C. The inner walls of the soft actuator conform to the shape of the pinch-grip mechanism of an actuated disposable instrument (e.g., forceps). The profile of the inner walls are designed to cause preferential expansion toward the instrument. An outer sheath made of paper is used to mitigate outward expansion of the outer wall. The soft actuators were fabricated with silicone elastomers of three different hardnesses (Dragon Skin 10, 20, and 30, Smooth-on Inc.), and two different values for the inner wall thickness d of 0.5 mm and 1 mm (see FIG. 4B). The soft actuator attached to an Alcon forceps weighs 10 g, which is approximately one third that of the stepper-motor-based forceps. FIG. 4C depicts a side section view of the soft actuator. The height of the channel is inversely proportional to the maximum pressure required for actuation A PD control system comprising two ON/OFF valves (MHJ series, Festo) and a pressure sensor was implemented to regulate the pressure inside the soft actuator. The controller converts the error in pressure for the soft actuator into a PWM signal that is used to control the valves. FIG. 4D shows that the maximum pressure required to completely close the forceps increases with the wall thickness and the elastomer hardness. A similar but counter-intuitive result was observed for the bandwidth for a full open-close cycle of the forceps (FIG. 4E). The bandwidth increases with an increase in the wall thickness and the elastomer hardness. This can be attributed to a decrease in the deflation time for the actuators when opening the forceps, with an increase in the wall thickness and the elastomer hardness. A version of the controller with a bandwidth of 2 Hz (measured by video analysis) and a resolution of 10 discrete steps between fully open and fully closed forceps was used for experiments.

The quick-change adapter and disposable-instrument actuators can be utilized with various manipulator kinematics, including many existing systems. Non-limiting examples of such systems include Johns Hopkins Steady-hand Robot, the TU Munich iRAM! S, etc. The manipulation system can also incorporate force-sensing instruments for improved safety. Examples disclosed of a telemanipulation system for retinal surgery can use unmodified commercially available instruments. The system is compact and light enough that it could reasonably be made head-mounted to passively compensate for various types of movements (e.g., head and eye movements). Two actuation mechanisms can enable examples of the system to use commercially available actuated instruments, and a quick-change instrument adapter can enable change of instruments during surgery.

The instrument actuation mechanisms and quick-change instrument adapter can be adapted to work with existing retinal-surgery systems.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

We claim:

1. An adapter system, comprising:
a set of adapters operably adapted to a set of microsurgical tools, wherein each adapter in the set of adapters is formed for a complimentary surgical tool in the set of surgical tools, each adapter having a setback feature, said setback feature designed to orient a corresponding tool tip at a common tip distance, wherein at least one of the adapters in the set of adapters includes a sleeve having a tool engagement surface and an adapter receptacle interface and one or more of:
the tool engagement surface is formed of multiple flexible parallel tabs circumferentially oriented about a tool location to engage the corresponding tool via an outer fastening compression nut,
the adapter receptacle interface includes an annular disk having complimentary threads which threadingly engage with threads of a receptacle, and
the setback feature is a radial protrusion extending inwardly from the sleeve along a primary axis of the adapter.

2. An adapter system according to claim 1, wherein the adapter system further comprises a receptacle having an operational connection mechanism attaching the adapter to the receptacle resulting in the common tip distance between the tool tip and the setback feature.

3. An adapter system according to claim 1, wherein the adapter system further comprises a first rotary input mechanism operably connected to a base plate, the first rotary input mechanism to receive a rotational input for transmission to an second rotary input mechanism, the second rotary input mechanism arranged to translate the rotational input from the first rotary input mechanism to a tool axis of each adapter.

4. An adapter system according to claim 1, wherein at least one of the adapters in the set of adapters is segmented to be compressed for applying a retention force on the tool for actuation thereof.

5. An adapter system according to claim 1, wherein the setback feature is a radial intrusion extending toward a primary axis of the adapter.

6. An adapter system according to claim 1, wherein each adapter is integrally formed with each complimentary tool.

7. An adapter system according to claim 1, wherein each adapter is removably coupleable with each complimentary tool.

8. An adapter system according to claim 1, wherein the common tip distance has a tolerance of less than 1 mm among the set of adapters.

9. An adapter system according to claim 3, wherein one or more of the first rotary transmission mechanism, the base plate, and interfacing components therebetween comprise a disposable polymer material.

10. An adapter system according to claim 9, wherein one or more of the first rotary transmission mechanism and base plate are attached to their respective proximal elements using magnetic coupling.

11. A system for a microsurgical tool, comprising:
an adapter receptacle which includes a yaw joint having a rotary motion translation mechanism and an adapter stop; and
the set of adapters according to claim 1, each adapter sized and shaped to be mated with the adapter stop such that the adapter facilitates transfer of tools into and out of the yaw joint.

12. The system as in claim 11, further comprising a receptacle retention platform which includes a base portion and a receptacle housing portion which rotatably retains the receptacle, and the base portion is connectable to a robotic manipulator arm.

13. The system as in claim 11, wherein the adapter has an inner diameter and an outer diameter each dimensioned such that the adapter is operably connectable to the tool and to the yaw joint.

14. A system for a microsurgical tool, comprising:
an adapter receptacle which includes a yaw joint having a rotary motion translation mechanism and an adapter stop; and
a set of adapters operably adapted to a set of microsurgical tools, wherein each adapter in the set of adapters is formed for a complimentary surgical tool in the set of surgical tools, each adapter having a setback feature, said setback feature designed to orient a corresponding tool tip at a common tip distance, each adapter sized and shaped to be mated with the adapter stop such that the adapter facilitates transfer of tools into and out of the yaw joint.

15. The system as in claim 14, further comprising a receptacle retention platform which includes a base portion and a receptacle housing portion which rotatably retains the adapter receptacle, and the base portion is connectable to a robotic manipulator arm and the adapter has an inner diameter and an outer diameter each dimensioned such that the adapter is operably connectable to the tool and to the yaw joint.

16. The system as in claim 14, wherein the adapter receptacle has an operational connection mechanism attaching the adapter to the adapter receptacle resulting in the common tip distance between the tool tip and the setback feature.

17. The system as in claim 14, wherein the adapter system further comprises a first rotary input mechanism operably connected to a base plate, the first rotary input mechanism to receive a rotational input for transmission to an second rotary input mechanism, the second rotary input mechanism arranged to translate the rotational input from the first rotary input mechanism to a tool axis of each adapter.

18. The system as in claim 17, wherein one or more of the first rotary transmission mechanism, the base plate, and interfacing components therebetween comprise a disposable polymer material.

19. The system as in claim 17, wherein one or more of the first rotary transmission mechanism and base plate are attached to their respective proximal elements using magnetic coupling.

20. The system as in claim 14, wherein the setback feature is a radial intrusion extending toward a primary axis of the adapter.

21. The system as in claim 14, wherein each adapter is integrally formed with each complimentary tool.

22. The system as in claim 14, wherein each adapter is removably coupleable with each complimentary tool.

23. The system as in claim 14, wherein the common tip distance has a tolerance of less than 1 mm among the set of adapters.

* * * * *